United States Patent [19]
Merger et al.

[11] 4,423,247
[45] Dec. 27, 1983

[54] MANUFACTURE OF ARALKYLARYLAMINES AND ALKYLARYLAMINES

[75] Inventors: Franz Merger, Frankenthal, Fed. Rep. of Germany; Ludwig Schroff, deceased, Ludwigshafen, Fed. Rep. of Germany, by Meinie Thea Schroff, heiress

[73] Assignee: BASF Aktiengesellschaft, Fed. Rep. of Germany

[21] Appl. No.: 944,292

[22] Filed: Sep. 21, 1978

Related U.S. Application Data

[63] Continuation of Ser. No. 781,148, Mar. 25, 1977, abandoned.

[30] Foreign Application Priority Data

Apr. 24, 1976 [DE] Fed. Rep. of Germany ....... 2618033

[51] Int. Cl.³ .............................................. C07C 87/28
[52] U.S. Cl. ................................ 564/391; 260/465 E; 560/19; 564/393

[58] Field of Search ............... 260/576, 578, 570.8 R, 260/462 E, 465 E; 564/391, 393; 560/19

[56] References Cited

U.S. PATENT DOCUMENTS 3,253,036  5/1966  Crawford ........................... 260/577

FOREIGN PATENT DOCUMENTS 50-93997  7/1975  Japan ............................... 260/570.8

OTHER PUBLICATIONS

Basic Principles of Organic Chemistry, Second Edition (1977) by John D. Roberts and Marjorie C. Caserio (pp. 1158 & 1159).
Kanji, "Chemical Abstracts", vol. 84, p. 479, Section No. 17416x, (1976).

Primary Examiner—Robert V. Hines
Attorney, Agent, or Firm—Keil & Witherspoon

[57] ABSTRACT

Aromatic amines are N-alkylated by reacting primary or secondary amines with dialkyl carbonates. The products are starting materials for the manufacture of dyes, crop protection agents and scents.

10 Claims, No Drawings

MANUFACTURE OF ARALKYLARYLAMINES AND ALKYLARYLAMINES

This is a continuation of application Ser. No. 781,148, filed Mar. 25, 1977 and now abandoned.

The present invention relates to a new process for N-alkylating aromatic amines by reacting primary or secondary aromatic amines with dialkyl carbonates.

Houben-Weyl, Methoden der Organischen Chemie, XI/1, pages 24 and 205, discloses that primary and secondary aromatic amines can be N-alkylated with alkyl esters of strong inorganic acids. The esters of sulfuric acid and of hydrohalic acids have attained particular importance in this respect. It has furthermore been disclosed that these amines can, in the presence of strong acids, also be reacted with alcohols (Houben-Weyl, loc. cit., page 134), with elimination of water, to give the corresponding alkylamines. However, all these processes suffer from certain disadvantages.

As an example, in the alkylation with esters of strong inorganic acids (for example dimethyl sulfate or methyl iodide) one equivalent of acid is liberated for each alkyl group introduced, and this acid must be removed by neutralizing. Furthermore, many of these alkylating agents, for example dimethyl sulfate, are extremely toxic.

The reaction of alcohols themselves with amines is unsatisfactory when carried out industrially, since the use of strong acids, e.g. sulfuric acid, presents difficulties from the point of view of corrosion of parts of the plant, difficulty of removing the catalyst, and, at times, sensitivity of other functional groups to hydrolysis.

German Laid-Open Application No. 2,160,111 discloses that aromatic amines, e.g. aniline, can be reacted with dialkyl carbonates, e.g. dimethyl carbonate, in the presence of Lewis acids as catalysts, to give carbamates, e.g. methyl N-phenyl-carbamate. The only by-products obtained in substantial amount are the substituted ureas for example diphenylurea. The said publication states that N-substituted amines, e.g. N-methylaniline, are only formed in small amounts as a by-product. If attempts are made (page 17) to react dimethyl carbonate with aniline in the molar ratio of 1:1 at 80° C. in the absence of a Lewis acid, no carbamate, and no substituted aniline, is produced even after 240 hours. If an excess of dimethyl carbonate is used, the same negative results are obtained. If the temperature is raised to 150° C., only traces of these compounds are obtained even after several hours.

We have found that aralkylarylamines and alkylarylamines are obtained in an advantageous manner by reacting amines with alkylating agents, if primary or secondary aromatic amines are reacted with diaralkyl carbonates or monodialkyl-monoalkyl carbonates or dialkyl carbonates at above 150° C. in the absence of catalytic amounts of a Lewis acid.

If aniline and dimethyl carbonate are used, the reaction can be represented by the following equation:

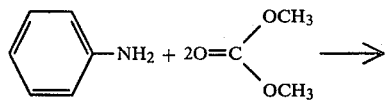

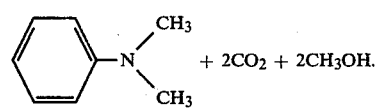

Compared to conventional processes, the process according to the invention gives, more simply and more economically, a large number of amines in good yield and high purity. It is not necessary to use catalysts. Involved isolation and neutralization operations, and corrosion problems, are avoided. Apart from the end product, all that is obtained is one mole of alcohol, and carbon dioxide, which is non-toxic; accordingly, the process according to the invention produces less pollution of the environment than do the conventional processes. The alcohol liberated can be reconverted by conventional methods, using CO and oxygen, and without using phosgene, to give dialkyl carbonate $$2ROH + CO + \tfrac{1}{2}O_2 \rightarrow O=C(OR)_2 + H_2O$$

(German Laid-Open Application No. 2,334,736). All these advantageous properties of the process according to the invention are surprising in view of the prior art and especially in view of German Laid-Open Application No. 2,160,111.

As the above German Laid-Open Application shows, it is essentially carbamate which is formed in the presence of catalytic amounts of a Lewis acid. Catalytic amounts of a Lewis acid are to be understood, in the present context, as the minimum amount in which the Lewis acid used acts as a catalyst for the manufacture of carbamate, and proportions by weight of Lewis acid above the minimum amount. The minimum amount is thus also the amount of Lewis acid which converts the amine predominantly, preferably to the extent of at least 50 percent of the total yield, based on starting material, into carbamate rather than into by-products such as urea and N-substituted amines; this very low minimum amount can readily be determined, from the carbamate yield obtained, by a few comparative experiments. It is true that proportions of Lewis acid which fall below the minimum amounts required for catalysis of the carbamates in the above manner (that is to say, in the sense of the above definition, non-catalytic amounts of a Lewis acid) can be used for the process according to the invention. However, the reaction in the absence of Lewis acid is of particular advantage and is at the same time generally the preferred embodiment of the process according to the invention.

The dialkyl carbonates can be manufactured in the conventional manner, for example by the process described in German Laid-Open Application No. 2,160,111 or, more advantageously, especially for reasons of protection of the environment, by reacting an alcohol with carbon monoxide and oxygen in the presence of copper catalysts, by the process described in German Laid-Open Application No. 2,334,736. The amine starting materials may carry several, advantageously from 1 to 4, and preferably 1 or 2, amino groups which are capable of reacting accordingly. Advantageous amines are those of the formula

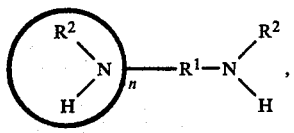

advantageous carbonates are those of the formula

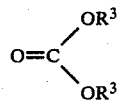

and, accordingly, advantageous end products are those of the formula

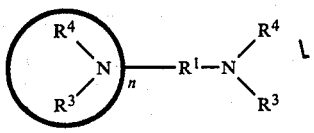

where $R^1$ is an aromatic radical, the individual radicals $R^2$ and $R^3$ may be identical or different and each is an araliphatic radical or especially an aliphatic radical, $R^2$ may also be hydrogen, $R^4$ has the same meanings as $R^2$ or $R^3$ and n is 0 or 1. Preferred starting materials I and II and, accordingly, preferred end products III are those where $R^1$ is naphthyl, naphthylene or, especially, phenylene or phenyl, the individual radicals $R^2$ and $R^3$ may be identical or different and each is aralkyl of 7 to 12 carbon atoms or, especially, alkyl of 1 to 7, advantageously of 1 to 4, carbon atoms, the above radicals being unsubstituted or substituted by groups and/or atoms which are inert under the reaction conditions, for example alkyl, alkoxy, each of 1 to 4 carbon atoms, carbalkoxy each of 2 to 4 carbon atoms, cyano, halogen, advantageously chlorine, or nitro, $R^2$ may also be hydrogen, $R^4$ has the meanings of $R^2$ or $R^3$ and n is 0 or 1. In the case of diamines or polyamines, the amino groups on the molecule may each carry the same or a different substituent and/or be unsubstituted.

The starting materials I are reacted with a stoichiometric amount, or an excess or a deficiency, of the starting materials II. In the case of the conversion of primary amines I to secondary amines III, from 0.1 to 0.9 mole of starting material II is used per mole of amino groups in starting material I, in the case of the conversion of secondary amines I to tertiary amines III, from 1 to 2.5 moles of starting material II are used per mole of amino groups in starting material I, and in the case of the conversion of primary amines I to tertiary amines III, from 2 to 5 moles of starting material II are used per mole of amino groups in starting material I. In the case of the reaction of primary amines I with aralkyl carbonates II to give secondary amines III, a ratio of from 1 to 2.5 moles of starting material II per mole of amino groups in starting material I is advantageous.

Examples of suitable starting materials I are unsubstituted aniline, aniline substituted in the 2-, 3- or 4-position by nitro, cyano, methyl, ethyl, n-propyl, isopropyl, n-butyl, isobutyl, sec.-butyl, tert.-butyl or chlorine; methoxyaniline, ethoxyaniline, n-propoxyaniline, isopropoxyaniline, n-butoxyaniline, isobutoxyaniline, sec.-butoxyaniline and tert.-butoxyaniline each substituted in the o-, m- oder p-position; methyl benzoate, ethyl benzoate, n-propyl benzoate, isopropyl benzoate, n-butyl benzoate, sec.-butyl benzoate, tert.-butyl benzoate and isobutyl benzoate each substituted by an amino group in the o-, m- or p-position; aniline disubstituted in the 2,4-, 2,5-, 2,6-, 2,3-, 3,4- or 3,5-position by the above substituents; α-naphthylamine and β-naphthylamine; o-, m- and p-phenylenediamine; 1,3-diaminobenzene substituted in the 2-position or 4-position, or 1,4-diaminobenzene substituted in the 2-position, by nitro, cyano, methyl, ethyl, n-propyl, isopropyl, n-butyl, isobutyl, sec.-butyl, tert.-butyl, chlorine, methoxy, ethoxy, n-propoxy, isopropoxy, n-butoxy, sec.-butoxy, tert.-butoxy, isobutoxy, carbmethoxy, carbethoxy, carb-n-propoxy, carbisopropoxy carb-n-butoxy, carb-sec.-butoxy, carb-tert.-butoxy or carbisobutoxy; 4,4'-diaminodiphenyl, 1,5-diaminonaphthalene, 1,8-diaminonaphthalene and o-dianisidine; and the above primary amines additionally substituted at the nitrogen by methyl, ethyl, n-propyl, isopropyl, n-butyl, sec.-butyl, tert.-butyl, isobutyl, benzyl or phenylethyl.

Preferred starting materials I are aniline, N-methylaniline, N-ethylaniline, o-, m- and p-toluidine, o-, m- and p-anisidine, o-, m- and p-chloroaniline, o-, m- and p-nitroanline, methyl o-, m- and p-aminobenzoate, 3-chloro-2-methylaniline, o-, m- or p-phenylenediamine, 2,4-toluylenediamine, 2,6-toluylenediamine, o-, m- and p-aminobenzonitrile, α-naphthylamine and β-naphthylamine.

Suitable starting materials II are dimethyl carbonate, diethyl carbonate, di-n-propyl carbonate, diisopropyl carbonate, di-n-butyl carbonate, di-sec.-butyl carbonate, di-tert.-butyl carbonate, diisobutyl carbonate, dibenzyl carbonate, methyl ethyl carbonate, methyl propyl carbonate and ethyl propyl carbonate; dimethyl carbonate, diethyl carbonate, di-n-propyl carbonate, methyl ethyl carbonate and dibenzyl carbonate are preferred.

The reaction is carried out at above 150° C., in general at from 150° C. to 350° C., preferably from 160° to 300° C., especially from 170° to 270° C., under atmospheric or superatmospheric pressure, preferably under the autogenous vapor pressure of the reaction mixture in the autoclave at the above temperatures, advantageously at from 1 to 200 bars, continuously or batchwise. Advantageously, the reaction mixture also serves as the solution medium or suspension medium. In such cases it is at times advantageous to add an excess of starting material II and/or to add, from the start, an additional amount of the alcohol which forms during the reaction. At times, especially in the case of high-melting amines, solvents which are inert under the reaction conditions can be used. Examples of suitable solvents are aromatic hydrocarbons, e.g. toluene, ethylbenzene, o-, m- and p-xylene, isopropylbenzene and methylnaphthalene, chlorobenzene, o- and m-dichlorobenzene, o-, m- and p-chlorotoluene and 1,2,4-trichlorobenzene; ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane and $\beta,\beta'$-dichlorodiethyl ether; aliphatic or cycloaliphatic hydrocarbons, e.g. heptane, nonane, gasoline fractions within a boiling range of from 70° to 190° C., cyclohexane, methylcyclohexane, decalin, petroleum ether, hexane, light naphtha, 2,2,4-trimethylpentane, 2,2,3-trimethylpentane, 2,2,3-trimethylpentane and octane; and mixtures of the above. Advantageously, from 100 to 2,000 percent by weight of solvent, based on starting material II, are used.

The reaction may be carried out as follows: a mixture of the starting materials I and II, with or without solvent, is kept at the reaction temperature for from 1 to 10 hours. The end product is then isolated from the mixture in the conventional manner, for example by fractional distillation.

The aralkylarylamines and alkylarylamines which may be manufactured by the process of the invention are valuable starting materials for the manufacture of dyes, crop protection agents and scents. For details of their use, reference may be made to the above publications and to Ullmanns Encyklopädie der technischen Chemie, Volume 19, pages 300–417.

In the Examples which follow, parts are by weight.

EXAMPLE 1

93 parts of aniline and 225 parts of dimethyl carbonate are heated in an autoclave at 200° C. for 5 hours. Excess dimethyl carbonate and methanol are distilled off under atmospheric pressure. Subsequent distillation under reduced pressure gives 115 parts of N,N-dimethylaniline (boiling point 81° C./15 mm Hg) which is 99 percent by weight pure. This corresponds to a yield of 95% of theory.

EXAMPLE 2

122 parts of 2,4-toluylenediamine and 450 parts of dimethyl carbonate are heated in an autoclave at 180° C. for 7 hours. Excess dimethyl carbonate and methanol are distilled off under atmospheric pressure. Subsequent distillation under reduced pressure gives 171 parts of N,N,N',N'-tetramethyltoluylenediamine (boiling point 77° C./0.4 mm Hg) which is 98 percent by weight pure. This corresponds to a yield of 96% of theory.

EXAMPLE 3

Per hour, 21 g of a solution of 3 parts of 2,4-toluylenediamine, 6 parts of methanol and 12 parts of dimethyl carbonate are passed through a 3 m long tubular reactor, of 6 mm diameter, at 210° C. and 120 bars. Analysis of the reaction product by gas chromatography shows that the conversion is 100%, based on 2,4-toluylenediamine. The yield of N,N,N',N'-tetramethyl-2,4-toluylenediamine is 3.06 g/hour=70% of theory. 1.08 g/hour (28% of theory) of dimethylamines and trimethylamines are obtained; these are reused and also converted to N,N,N',N'-tetramethyltoluylenediamine.

EXAMPLES 4 TO 19

The Examples which follow are carried out as described for Example 1, with 120 parts of amine and under the conditions shown in the Table.

TABLE

| Example No. | Carbonate starting material | Amine starting material | Reaction temperature, °C. | Reaction time in hours | Equivalent ratio of amine:carbonate | End product | Yield, % of theory |
|---|---|---|---|---|---|---|---|
| 4 | dimethyl carbonate | p-toluidine | 200 | 4 | 1:3 | N,N—dimethyl-p-toluidine | 98 |
| 5 | dimethyl carbonate | o-anisidine | 200 | 5 | 1:2.5 | N,N—dimethyl-o-anisidine | 70 |
| 6 | dimethyl carbonate | m-anisidine | 200 | 5 | 1:2.5 | N,N—dimethyl-m-anisidine | 97 |
| 7 | dimethyl carbonate | p-phenylenediamine | 200 | 3.5 | 1:5.4 | N,N,N',N'—tetramethyl-p-phenylenediamine | 98.5 |
| 8 | dimethyl carbonate | o-phenylenediamine | 200 | 5 | 1:4 | N,N,N',N'—tetramethyl-o-phenylenediamine | 40 |
|  |  |  |  |  |  | trimethyl- and dimethyl-o-phenylenediamines | 30 |
| 9 | dimethyl carbonate | methyl o-aminobenzoate | 250 | 5.5 | 1:4 | N,N—dimethyl methyl o-aminobenzoate | 55 |
| 10 | dimethyl carbonate | methyl m-aminobenzoate | 250 | 4 | 1:4 | N,N—dimethyl methyl m-aminobenzoate | 92 |
| 11 | dimethyl carbonate | o-chloroaniline | 250 | 5 | 1:2.5 | N,N—dimethyl-o-chloroaniline | 67 |
| 12 | dimethyl carbonate | m-chloroaniline | 250 | 5 | 1:2.5 | N,N—dimethyl-m-chloroaniline | 86 |
| 13 | dimethyl carbonate | m-nitroaniline | 220 | 10 | 1:2.5 | N,N—dimethyl-m-nitroaniline | 48 |
| 14 | dimethyl carbonate | N—ethylaniline | 220 | 5 | 1:2 | N—ethyl-N—methylaniline | 60 |
| 15 | dimethyl carbonate | 1-aminonaphthalene | 230 | 5 | 1:5 | N,N—dimethyl-1-aminonaphthalene | 79 |
| 16 | dimethyl carbonate | 1,8-diaminonaphthalene | 200 | 5 | 1:5 | tetramethyl-1,8-diaminonaphthalene | 65 |
|  |  |  |  |  |  | trimethyl- and dimethyl-1,8-diaminonaphthalenes | 7 |
| 17 | diethyl carbonate | p-toluidine | 230 | 5 | 1:2.25 | N—ethyl-p-toluidine | 60 |
|  |  |  |  |  |  | N,N—diethyl-p-toluidine | 25 |
| 18 | diethyl carbonate | p-phenylenediamine | 220 | 5 | 1:6.4 | tetraethyl-p-phenylenediamine | 31 |
|  |  |  |  |  |  | triethyl-p-phenylenediamine | 35 |
|  |  |  |  |  |  | diethyl-p-phenylenediamine | 28 |
|  |  |  |  |  |  | ethyl-p-phenylenediamine | 5 |
| 19 | dibenzyl | p-toluidine | 230 | 5 | 1:2.25 | N—benzyl-p-toluidine | 54 |

We claim:
1. A process for the manufacture of aralkylarylamines and alkylarylamines which comprises:
reacting at a temperature above 150° C. in the absence of catalytic amounts of Lewis acid a primary or secondary amine of the formula

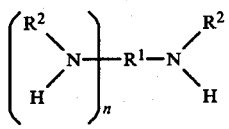  I with a carbonate of the formula

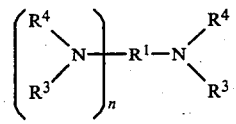  II where $R^1$ is naphthyl, naphthylene, phenyl or phenylene and the individual radicals $R^2$ and $R^3$ are identical or different and each is aralkyl of 7 to 12 carbon atoms or alkyl of 1 to 7 carbon atoms, said radicals $R^2$ and $R^3$ being unsubstituted or substituted by alkyl of 1 to 4 carbon atoms, alkoxy of 1 to 4 carbon atoms, carbalkoxy each of 2 to 4 carbon atoms, cyano, halogen or nitro, $R^2$ may also be hydrogen and n is 0 or 1, to form an aralkylarylamine or alkylarylamine of the formula $$\left( \begin{array}{c} R^4 \\ \diagdown \\ R^3 \diagup \end{array} N \!-\! R^1 \!-\! N \begin{array}{c} R^4 \\ \diagdown \\ \diagup R^3 \end{array} \right)_n$$  III where $R^1$ and $R^3$ are defined as above, $R^4$ has the meanings of $R^2$ or $R^3$ and n is 0 or 1.

2. A process as set forth in claim 1, wherein the mixture of starting materials I and II is kept at the reaction temperature for from about 1 to 10 hours.

3. A process as set forth in claim 1 wherein a primary aromatic amine is converted into a secondary amine employing from 0.1 to 0.9 mole of carbonate per mole of amino groups in the primary amine.

4. A process as set forth in claim 1 wherein a secondary aromatic amine is converted into a tertiary amine employing from 1 to 2.5 moles of carbonate per mole of amino groups in the secondary amine.

5. A process as set forth in claim 1 wherein a primary aromatic amine is converted into a tertiary amine employing from 2 to 5 moles of carbonate per mole of amino groups in the primary amine.

6. A process as set forth in claim 1, wherein a primary aromatic amine is reacted with a dialkyl carbonate to give a secondary amine employing from 1 to 2.5 moles of dialkyl carbonate per mole of amino groups in the primary amine.

7. A process as set forth in claim 1, wherein the reaction is carried out at from above 150° to 350° C.

8. A process as set forth in claim 1, wherein the reaction is carried out at from above 160° to 300° C.

9. A process as set forth in claim 1, wherein the reaction is carried out at from above 170° to 270° C.

10. A process as set forth in claim 1, wherein the reaction is carried out in the presence of solvents which are inert under the reaction conditions.

* * * * *

UNITED STATES PATENT AND TRADEMARK OFFICE
CERTIFICATE OF CORRECTION

PATENT NO. : 4,423,247
DATED : December 27, 1983
INVENTOR(S) : Franz MERGER et al.

It is certified that error appears in the above-identified patent and that said Letters Patent is hereby corrected as shown below:

Claim 8, column 8, line 2, change "above 160° to 300°C" to --about 160° to 300°C--.

Claim 9, column 8, line 2, change "above 170° to 270°C" to --about 170° to 270°C--.

Signed and Sealed this

Tenth Day of April 1984

[SEAL]

Attest:

Attesting Officer

GERALD J. MOSSINGHOFF
Commissioner of Patents and Trademarks